United States Patent
Fenton

(10) Patent No.: US 8,328,779 B2
(45) Date of Patent: Dec. 11, 2012

(54) LOCATING FLANGE FOR A TWO-PIECE OSTOMY ADHESIVE MOUNT

(75) Inventor: Gary H. Fenton, Pepper Pike, OH (US)

(73) Assignee: Marlen Manufacturing & Development, Inc., Bedford, OH (US)

( * ) Notice: Subject to any disclaimer, the term of this patent is extended or adjusted under 35 U.S.C. 154(b) by 618 days.

(21) Appl. No.: 12/469,126

(22) Filed: May 20, 2009

(65) Prior Publication Data

US 2009/0299309 A1 Dec. 3, 2009

Related U.S. Application Data

(60) Provisional application No. 61/057,391, filed on May 30, 2008.

(51) Int. Cl.
*A61F 5/44* (2006.01)

(52) U.S. Cl. ........ 604/336; 604/332; 604/337; 604/338; 604/342; 604/343; 604/344; 604/345

(58) Field of Classification Search .................. 604/336, 604/332, 338, 337, 342, 343, 344, 345, 339
See application file for complete search history.

(56) References Cited

U.S. PATENT DOCUMENTS

| | | | | |
|---|---|---|---|---|
| 3,762,412 A | * | 10/1973 | Frank | 604/338 |
| 3,964,485 A | | 6/1976 | Neumeier | |
| 4,219,023 A | * | 8/1980 | Galindo | 604/344 |
| 4,551,590 A | * | 11/1985 | Mahon | 200/38 R |
| 4,610,676 A | * | 9/1986 | Schneider et al. | 604/339 |
| 4,636,206 A | * | 1/1987 | Ederati et al. | 604/340 |
| 4,775,374 A | * | 10/1988 | Cilento et al. | 604/344 |
| 4,834,731 A | * | 5/1989 | Nowak et al. | 604/339 |
| 4,872,869 A | * | 10/1989 | Johns | 604/342 |
| 5,125,917 A | * | 6/1992 | Whealin | 604/340 |
| 5,139,492 A | * | 8/1992 | Leise et al. | 604/339 |
| 5,185,008 A | * | 2/1993 | Lavender | 604/338 |
| 5,257,981 A | * | 11/1993 | Takahashi | 604/342 |
| 5,261,708 A | * | 11/1993 | Steer | 285/319 |

(Continued)

FOREIGN PATENT DOCUMENTS

EP 0 276 898 A2 * 8/1988

(Continued)

OTHER PUBLICATIONS

International Search Report for PCT/US2009/045410 dated Jan. 12, 2010.

*Primary Examiner* — Kevin C Sirmons
*Assistant Examiner* — Ginger T Chapman
(74) *Attorney, Agent, or Firm* — Pearne & Gordon LLP

(57) ABSTRACT

A mounting assembly for an ostomy pouch. The assembly includes a body flange having an adhesive coating on one side adapted to be adhered to the peristomal skin surface of an osteomate. Diametrically opposed loops project from the edge of the flange and form pockets. Also included is an ostomy pouch having a stoma receiving opening surrounded by a stiffly flexible ring having diametrically opposed loops that cooperate with the pockets on the flange loops. An adhesive coating is provided on the flexible ring and there is a mechanical interlock between the ring and flange. When the loops on the flexible ring are aligned with the pockets on the flange the flange and ring may be adhesively interlocked to attach the pouch to the body flange.

9 Claims, 3 Drawing Sheets

U.S. PATENT DOCUMENTS

| | | | |
|---|---|---|---|
| 5,520,670 A * | 5/1996 | Blum | 604/338 |
| 5,549,588 A * | 8/1996 | Johnsen | 604/339 |
| 5,830,200 A * | 11/1998 | Steer et al. | 604/338 |
| 5,843,053 A * | 12/1998 | Steer | 604/342 |
| 5,947,941 A * | 9/1999 | Leise et al. | 604/338 |
| 6,293,930 B1 | 9/2001 | Brunsgaard et al. | |
| 6,537,261 B1 * | 3/2003 | Steer et al. | 604/342 |
| 7,422,578 B2 * | 9/2008 | Shan et al. | 604/342 |
| 2007/0260206 A1 | 11/2007 | Mullejans et al. | |

FOREIGN PATENT DOCUMENTS

| | | | |
|---|---|---|---|
| GB | 2 177 924 A * | 2/1987 | |

\* cited by examiner

LOCATING FLANGE FOR A TWO-PIECE OSTOMY ADHESIVE MOUNT

RELATED APPLICATIONS

This application claims the benefit of U.S. Provisional Application No. 61/057,391, filed on May 30, 2008, the entire disclosure of which is hereby incorporated herein by reference.

BACKGROUND OF THE INVENTION

1. Field of the Invention

This invention relates to a two-piece mounting assembly for an ostomy pouch and, more particularly, to a locating arrangement for an adhesively coupled two-piece mounting assembly. The assembly includes a body flange piece which is adhesively bonded to the peristomal skin surfaces of an osteomate. A pouch is in turn adhesively bonded to the body flange piece. The arrangement allows the osteomate to change bags several times without removing the body flange piece.

2. Brief Description of the Invention

This invention provides a convenient interlock between the body flange piece and the pouch so that these units may be properly aligned prior to bonding. The interlock includes diametrically arranged loops on the body flange and corresponding diametrically aligned loops on the pouch. One set of diametrically aligned loops is provided with pockets on one face and another set of diametrically aligned loops is dimentioned to fit within the pockets to provide the interlock. When the loops are snapped together, pressure may be applied to the adhesive interface between the body flange and the pouch to secure these members.

An ostomy belt may be employed as added security to hold the mounting assembly in place. Clips on the belt pass through the aligned loops to retain the assembly as a unit.

DETAILED DESCRIPTION OF THE DRAWINGS

Figure 1:
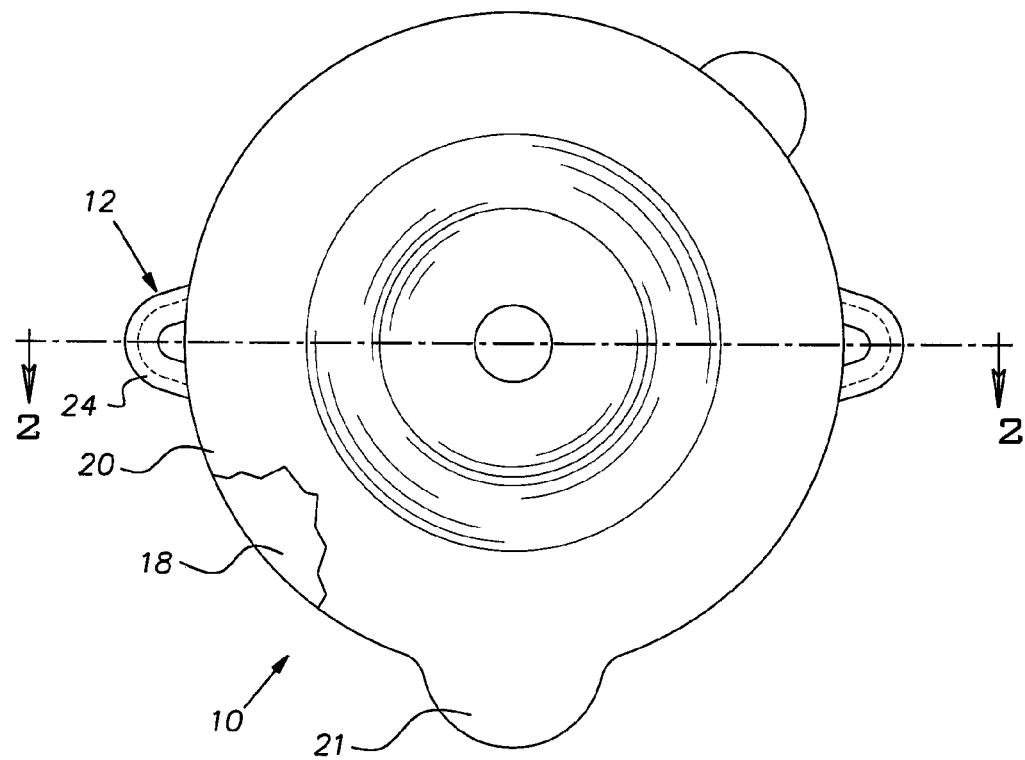
FIG. 1 is a top view of a mounting flange.
Figure 2:
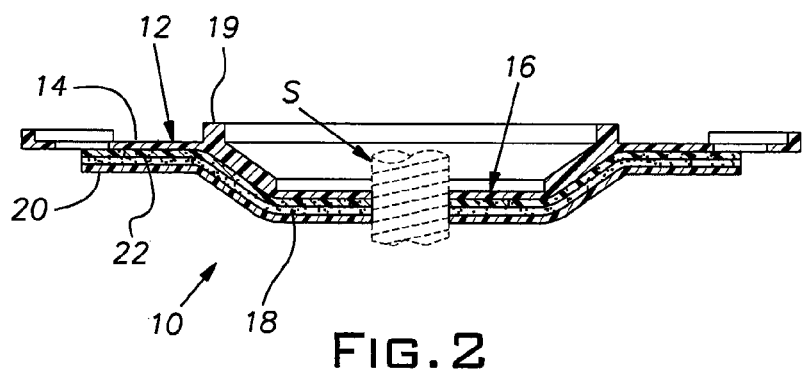
FIG. 2 is a sectional view, the plane of the section being indicated by the line 2-2 in FIG. 1.
Figure 3:
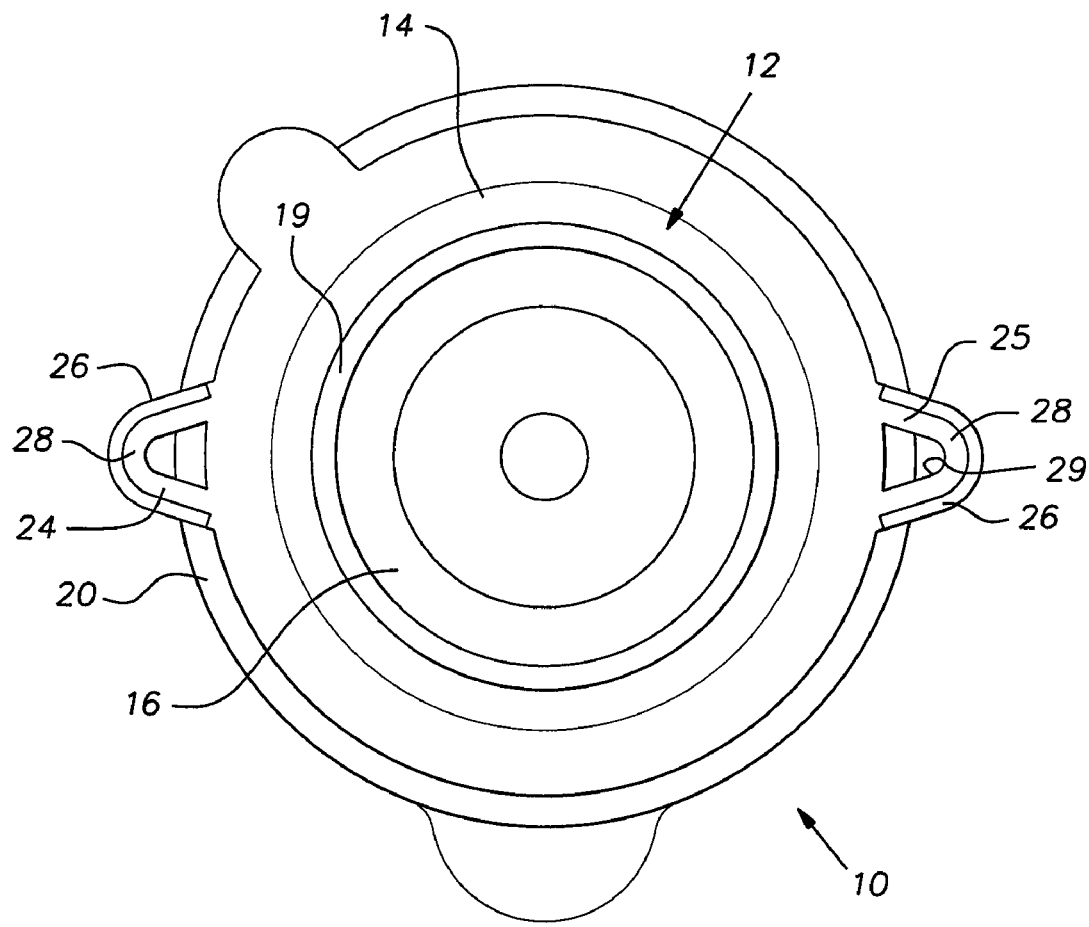
FIG. 3 is a bottom view of the mounting flange.

Referring to FIGS. 1-3, there is illustrated a body flange 10 adapted to be affixed to the peristonal skin surface and surround the stoma S of an osteomate. The flange 10 comprises a stiffly flexible plastic base portion 12 having a rim 14 and a central dome 16, as may be seen in FIG. 2. A ring 19 projects from the dome bottom.

An adhesive layer 18 covers the top of the flange 10 and is preferably a hydrocolloid-containing adhesive capable of absorbing moisture and having both wet and dry tack. A release liner 20 covers the layer 18 and has a tab 21 permitting ease of removal. A foam layer 22 is interposed between the adhesive layer 18 and the flange 10.

The flange 10 further includes diametrically opposed first and second loops 24 and 25. Each loop is provided with a fence 26 which forms a pocket 28 on the loops 24 and 25.

Figure 4:
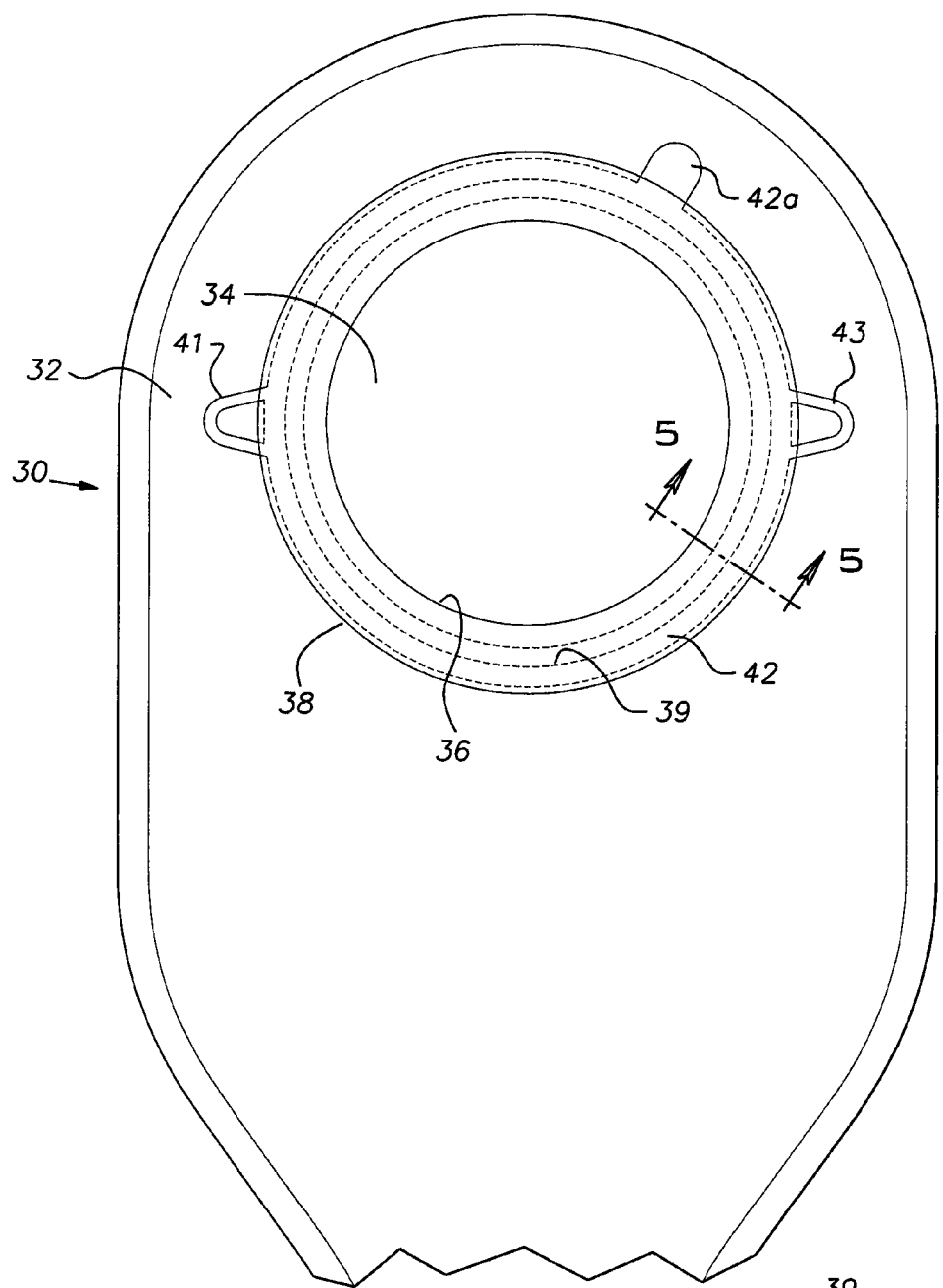
FIG. 4 is a view of a pouch.
Figure 5:
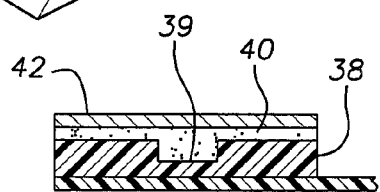
FIG. 5 is a sectional view, the plane of the view. Being indicated by the line 5-5 in FIG. 4.

Referring now to FIGS. 4 and 5, there is illustrated a pouch 30 formed by inner and outer plastic walls 32 and 34 respectively. The walls 32 and 34 are sealed at their edges to form a stoma receiving pouch. An aperture 36 is provided in the wall 32 and a stiffly flexible plastic ring 38 surrounds the aperture 36.

The ring 38 is provided with a central groove 39 and a pair of diametrically opposed ring tabs 41 and 43 surrounds the aperture. An adhesive coating 40 covers the ring 38 and the coating, in turn, is covered by a release liner 42.

With the flange 10 in place on the skin of the osteomate and with the liner 42 on the adhesive 40 removed, the third and fourth loops 41 and 43 are grasped and the third and fourth loops 41 and 43 are snapped into the pockets 28. When the third and fourth loops 41 and 43 are in place, the ring 19 is aligned with the groove 39 and will enter the groove 39. When the body flange 10 needs to be replaced, it may be peeled off by grasping a tab 42a (FIG. 4).

What is claimed is:

1. A mounting assembly for an ostomy pouch comprising a body flange having an adhesive coating on one side, which is adapted to be bonded to the peristomal skin surface of an osteomate, the body flange having an axially projecting ring on another side and at least one first and second loops diametrically projecting from an edge of such flange, said first and second loops having a raised fence around an opening in the first and second loops which forms a pocket, an ostomy pouch formed by inner and outer walls, said inner wall having an aperture therein with a stiffly flexible ring encircling said aperture, diametrically projecting third and fourth loops extending from an edge of said ring, a concentric groove in said flexible ring an adhesive coating in said groove, said third and fourth loops being engageable within the pocket of said first and second loops to align said ring of said body flange with the concentric groove in said flexible ring.

2. A mounting assembly according to claim 1, wherein said body flange has a rim and a central dome.

3. A body flange according to claim 2, wherein a foam layer is provided on the flange between the flange and the adhesive coating.

4. A mounting assembly according to claim 1, wherein the adhesive coating on said body flange is a hydrocolloid-containing adhesive capable of adsorbing water and having wet and dry tack.

5. A mounting assembly according to claim 1, wherein said first and second loops are diametrically opposed loops and said third and fourth loops are diametrically opposed.

6. A mounting assembly for an ostomy pouch comprising a body flange having an adhesive coating on one side which is adapted to be bonded to the peristomal skin surface of an osteomate, the body flange having an axially projecting ring and a pair of diametrically opposed first and second loops projecting from opposite edges of the flange, said loops having a raised fence around an opening in the loop which forms a pocket, an ostomy pouch formed by inner and outer walls, said inner wall having an aperture therein with a stiffly flexible ring encircling said aperture, a pair of diametrically opposed third and fourth loops projecting from opposite edges of said ring, a concentric groove in said flexible ring an adhesive coating in said groove, said groove receiving said ring of said flange and adhesively retaining it and said third and fourth loops being engaged within the pockets of said first and second loops.

7. A mounting assembly according to claim 6, wherein said body flange has a rim and a central dome.

8. A mounting flange according to claim 6, wherein a foam layer is provided on the flange between the flange and the adhesive coating.

9. A mounting flange assembly according to claim 6, wherein the adhesive coating on said flange is a hydrocolloid-containing adhesive capable of adsorbing water and having wet and dry tack.

* * * * *